(12) United States Patent
Shostak et al.

(10) Patent No.: US 9,265,174 B2
(45) Date of Patent: Feb. 16, 2016

(54) METHOD AND APPARATUS FOR OPTIMIZING GERMICIDAL LAMP PERFORMANCE IN A DISINFECTION DEVICE

(71) Applicants: Aleksandr Shostak, Northridge, CA (US); Ashish Mathur, Santa Clara, CA (US); Richard Hayes, Thousand Oaks, CA (US); Peter Veloz, Glendale, CA (US); David Witham, Ventura, CA (US); Filiberto Betancourt, North Hills, CA (US); Lev Rotkop, Beverly Hills, CA (US)

(72) Inventors: Aleksandr Shostak, Northridge, CA (US); Ashish Mathur, Santa Clara, CA (US); Richard Hayes, Thousand Oaks, CA (US); Peter Veloz, Glendale, CA (US); David Witham, Ventura, CA (US); Filiberto Betancourt, North Hills, CA (US); Lev Rotkop, Beverly Hills, CA (US)

(73) Assignee: ULTRAVIOLET DEVICES, INC., Valencia, CA (US)

( * ) Notice: Subject to any disclaimer, the term of this patent is extended or adjusted under 35 U.S.C. 154(b) by 0 days.

(21) Appl. No.: 14/325,357

(22) Filed: Jul. 7, 2014

(65) Prior Publication Data
US 2015/0115170 A1    Apr. 30, 2015

Related U.S. Application Data

(60) Provisional application No. 61/895,010, filed on Oct. 24, 2013.

(51) Int. Cl.
*A61L 2/10*  (2006.01)
*H05K 7/20* (2006.01)
*A61L 9/20*  (2006.01)

(52) U.S. Cl.
CPC .............. *H05K 7/20136* (2013.01); *A61L 2/10* (2013.01); *A61L 9/20* (2013.01); *H05K 7/20436* (2013.01)

(58) Field of Classification Search
USPC ...... 250/493.1, 494.1, 504 R, 504 H; 422/20, 422/21, 22, 24
See application file for complete search history.

(56) References Cited

U.S. PATENT DOCUMENTS

| | | | |
|---|---|---|---|
| 2,932,753 | A | 4/1960 | Arnott |
| 3,957,328 | A | 5/1976 | Van Der Wolf |
| 5,112,370 | A | 5/1992 | Gazzano |
| 5,372,781 | A | 12/1994 | Hallett |
| 6,322,614 | B1 | 11/2001 | Tillmans |
| 6,610,990 | B1 | 8/2003 | Morruzzi |
| 6,656,424 | B1 | 12/2003 | Deal |
| 6,911,177 | B2 | 6/2005 | Deal |
| 7,005,111 | B2 | 2/2006 | Bollini |
| 7,175,814 | B2 | 2/2007 | Dionisio |
| 7,459,694 | B2 | 12/2008 | Scheir |
| 7,658,891 | B1 | 2/2010 | Barnes |
| 7,816,849 | B2 | 10/2010 | Pirovic |
| 8,167,542 | B1 | 5/2012 | Owusu |
| 8,318,007 | B2 | 11/2012 | Fraser |
| D684,671 | S | 6/2013 | Betancourt |
| 8,455,832 | B2 | 6/2013 | Statham |
| 8,791,441 | B1 | 7/2014 | Lichtblau |
| 2004/0170526 | A1 | 9/2004 | Curry |
| 2005/0258378 | A1 | 11/2005 | Speer |
| 2006/0145092 | A1 | 7/2006 | Gunn |
| 2006/0278075 | A1 | 12/2006 | Blackner |

(Continued)

*Primary Examiner* — Nicole Ippolito
(74) *Attorney, Agent, or Firm* — Law Office of David Hong

(57) ABSTRACT

This invention controls the temperature of the critical spot of the UV lamps and on the critical spots having a deposit of mercury or amalgam containing mercury by directing a uniform flow of air on and around the critical spots having amalgam or be other means to remove heat from the critical spots.

16 Claims, 6 Drawing Sheets

(56) References Cited

U.S. PATENT DOCUMENTS

| | | |
|---|---|---|
| 2009/0090667 A1 | 4/2009 | Fraser |
| 2010/0028134 A1 | 2/2010 | Slapak |
| 2010/0104471 A1 | 4/2010 | Harmon |
| 2012/0246863 A1 | 10/2012 | Douglas |
| 2012/0305787 A1* | 12/2012 | Henson .................... A61L 2/10 250/372 |
| 2013/0020942 A1 | 1/2013 | Voronov |
| 2013/0119851 A1 | 5/2013 | Nakamura |
| 2013/0126760 A1 | 5/2013 | Klein |

* cited by examiner

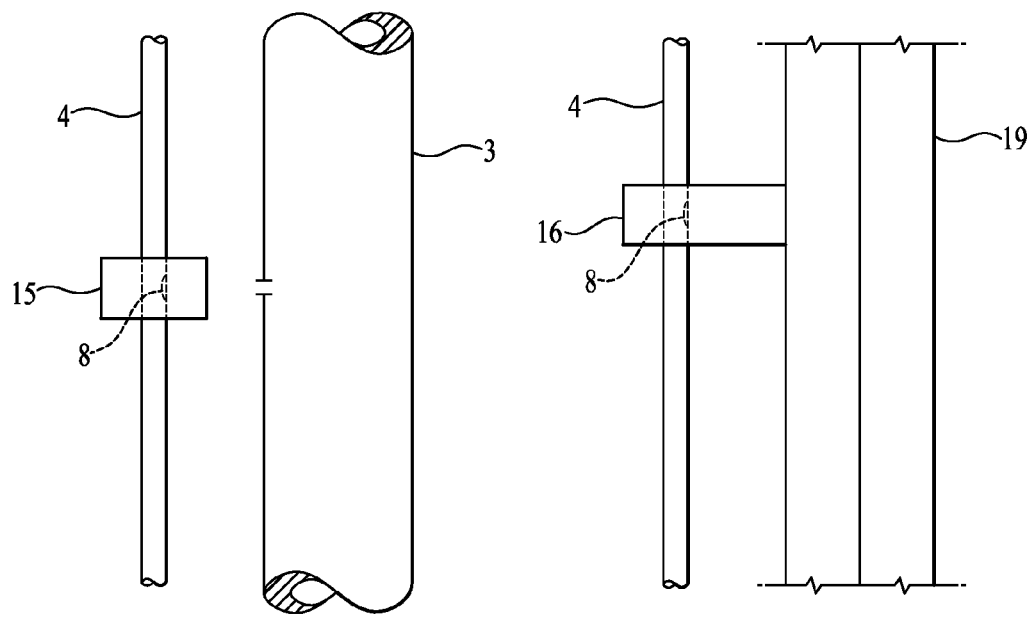
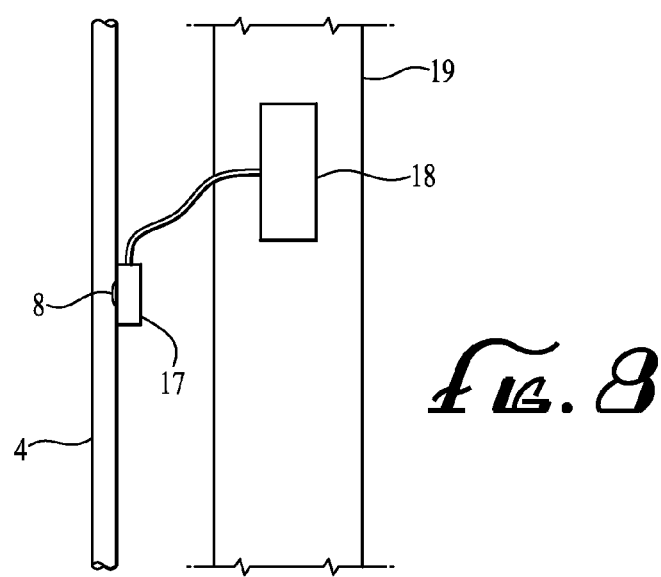

METHOD AND APPARATUS FOR OPTIMIZING GERMICIDAL LAMP PERFORMANCE IN A DISINFECTION DEVICE

PRIORITY CLAIM

This application claims the benefit of U.S. Provisional Patent Application No. 61/895,010, filed on Oct. 24, 2013, which is incorporated by reference in entirety. This application is also related to U.S. Design Pat. No. D684,671, which was issued on Jun. 19, 2013, which is also incorporated by reference in entirety.

BACKGROUND OF THE INVENTION

The effectiveness of germicidal ultraviolet (UV-C) irradiation as a powerful disinfecting technology has been well documented in peer-reviewed literature as well as in practice. Germicidal UV-C disinfection has been used for decades in disinfecting municipal drinking water, waste water, and in air and surface applications to disinfect against various micro-organisms such as bacteria, virus and mold. UVC devices employ one or more lamps emitting a spectral wavelength output of approximately 254 nm which disrupts the DNA structure of the micro-organisms, rendering them harmless and unable to reproduce.

The lamps typically used in these devices are low pressure mercury vapor discharge lamps. There are three basic types of low pressure ultraviolet lamps in commercial use. A standard output lamp, with input of approximately 425 milliamps has been used for many years. For about two decades, a higher output type lamp with an input of about 850 milliamps has been utilized. Recently a very high output lamp with an input current of from 2.0 to as high as 8.0 amps has become popular in some types of disinfection application. Applications of this type of lamp are popular where high levels of UVC are required such as in municipal water treatment plants.

Construction of the lamp and the materials used are somewhat different to accommodate the high temperatures. With the standard and high output lamps, pure mercury is generally used in the lamp to generate the UVC wavelength of approximately 254 nm. In the very high output lamp, generally the mercury is supplied in an amalgam of metals and may be located on one or more spots placed on the inside of the lamp envelope.

The necessary relatively high doses of ultraviolet radiation typically required to achieve desired disinfection levels requires the use of multiple germicidal lamps. The use of multiple germicidal lamps increases expenses, as well as maintenance. Therefore, it is desirable to use fewer very high output germicidal lamps.

However, applying a very high output germicidal lamp, particularly in air, is not without difficulties. During operation of a low pressure mercury vapor discharge lamp, the vapor pressure of the mercury greatly affects lamp output. For an efficient operation of the lamp, a predetermined range of the mercury vapor pressure inside the discharge vessel is required.

By using an amalgam containing mercury, the mercury vapor pressure can be controlled within this predetermined range for a relatively broad temperature range, allowing operating the lamp at a high efficiency and to deliver a relatively high radiation output within this temperature range. Very high output amalgam lamps thus provide the highest UVC output amongst low pressure mercury lamps and are therefore highly desirable for use for disinfection applications.

The mercury or amalgam of mercury may be located in many different places. In many lamps, it is typically located in one or more locations of the glass inner surface facing the discharge space of the low-pressure mercury vapor discharge lamp. As a result, the amalgam is exposed directly to the discharge space so that the temperature of the amalgam can increase relatively rapidly after the discharge lamp is turned on or lit up. The ideal operating temperature range for germicidal amalgam lamps can vary due to the composition of the amalgam. Typically, it is from 80 degrees C. to 140 degrees C.

However, the higher temperatures occurring at high loading of the lamp may cause the temperature of the amalgam to exceed the maximum operating temperature. This high temperature is not generally a problem when very high output lamps are used for water treatment. In this application, the lamps are generally housed in a quartz sleeve and submerged in moving water, which allows cooling of the lamp and maintains the temperature within the proper temperature range. This is most likely the reason that most applications of very high output lamps are limited to water treatment applications only.

Currently, there are little or no applications of very high output lamps in ambient air. In this air application, the temperature at the amalgam spot can exceed 150 degrees C. If the amalgam melts, several things may happen. The amalgam may move out of position and could make contact with an electrode and cause possible shorting or ineffective operation of the lamp. The molten amalgam material may be spread throughout the lamp and solidify at those positions when the operating conditions change. Solidified amalgam material at a position within the discharge path, for example, may become too hot at a later stage of the lamp use, i.e. the amalgam temperature will become outside its temperature range. When the amalgam is operating outside its ideal temperature range, this results in too high a mercury vapor pressure and hence reduces the lamp efficiency.

The positioning of the (germicidal) lamp, i.e. horizontal versus vertical positioning of the lamp, also influences the temperature of the amalgam. If the system design and application do not allow the amalgam to get into their proper operating temperature range, the lamp will have very low UV output and tend to be quite unstable.

Amalgam lamps provide the highest UVC output amongst low pressure mercury lamps and are therefore highly desirable for use in disinfection applications. However, due to the susceptibility of the amalgam to melt when the temperature exceeds the operating range, the use of germicidal amalgam lamps has been almost exclusively limited to water or liquid disinfection applications, wherein the amalgam lamps are constantly submerged in water or liquids, allowing the lamps to operate in the ideal temperature range.

It is the purpose of this invention to solve these temperature problems for air and surface disinfection applications.

SUMMARY OF THE INVENTION

It is highly desirable to be able to utilize germicidal lamps and in particular very high output germicidal lamps for air and surface applications. The present invention discusses a novel approach to utilize the very high UVC output of germicidal amalgam lamps in UVC disinfection devices in air and surface applications by providing a means to reduce and/or control the temperature of the amalgam spot(s) thus allowing the lamp to operate in its ideal operating range.

Another object of this invention is to allow the use of the germicidal amalgam lamp for use in a vertical configuration in a UVC disinfection device by ensuring that the amalgam is kept in its position and operating within the ideal temperature range. Yet another object of this invention is to reduce or eliminate the possibility of the amalgam melting. The present invention allows the germicidal amalgam lamps to be used in devices for air and surface disinfection where the amalgam lamp is exposed to ambient air. The invention discloses a novel approach to cool and/or control the temperature of the amalgam spot, thereby preventing the amalgam spot from melting and allowing the lamp to operate in an ideal operating temperature range and deliver maximum UVC output.

An example of a UVC disinfection device is the V-360+ mobile disinfection device, by UltraViolet Devices, Inc., which is used to disinfect surfaces in a healthcare environment. It is therefore highly desirable to utilize amalgam lamps to maximize the UVC output of the V360+ device and allow rapid disinfection times. The V-360+ device (See FIG. 1) utilizes more than one or four germicidal amalgam lamps which are located around a highly reflective hollow cylindrical aluminum support/conduit mounted at the center of a circular base. The combination of the high output amalgam lamps and the highly reflective support allows the V360+ device to deliver a high dose of UVC in order to achieve high levels of disinfections and rapid disinfection times.

However, with the lamps positioned in a vertical configuration, the amalgam spots are highly susceptible to overheating and even melting and moving out of position due to conditions described previously.

When the device is used in a typical ambient environment, the temperature of the critical spots (amalgam) can exceed 150 degrees C. and make the lamp operate outside its ideal operating range. The proximity of these lamps to the aluminum support lends to even higher temperature at the amalgam spot or spots.

This invention overcomes this challenge by providing an effective method to control the temperature of the critical spot(s) of the lamps on this device. In one embodiment of the application, the temperature of the critical spot (amalgam) is maintained by directing a uniform flow of air on and around the critical spot or spots (amalgam). The flow of air is generated by a fan located inside the V-360+, whereby the flow of air is directed to the critical spot (amalgam) through apertures located on the cylindrical conduit in close proximity to the spot or spots. The size of the cooling fan, location on the cylindrical conduit and the size of the apertures are judiciously chosen to provide an optimal amount of air flow through the apertures on the cylindrical conduit.

The air flow obtained through this arrangement is such that it provides an optimal amount of cooling in order maintain the temperature of the amalgam spot or spots in the ideal operating range, approximately between 80 deg C. and 140 deg C.

In another embodiment of the application, air flow is provided to the amalgam spot or spots through the use of air distribution nozzles that are mounted on the support and/or conduit in close proximity to the critical spot or spots, wherein the air flow is generated by the fan located optimally inside the device.

In another embodiment of the application, air flow is provided to the amalgam spot(s) via air diverter tubes that are mounted inside the support/conduit in close proximity to the amalgam spot or spots and divert an optimal amount of air onto the amalgam spot or spots.

In another embodiment of the application, the temperature of the critical spot or points is controlled by the use of a heat sink that is mounted on the critical spot or points and is connected to the support. By transferring the excess heat to the support, the heat sink maintains the temperature of the critical spot or spots (amalgam) in the desired operating range.

In yet another embodiment, a thermoelectric device is affixed to the critical spots (amalgam) of the lamp and is used to control the temperature of the critical spot. The thermoelectric device may be controlled to maintain a pre-determined temperature, within the ideal temperature range. A temperature sensing device may also be used by the controller.

BRIEF DESCRIPTION OF THE DRAWINGS

FIG. 6. A side view of an alternate embodiment incorporating heat sinks attached to the UV lamp.

FIG. 7. A side view of an alternate embodiment with a heat sink attached to the UV lamp and in contact with a structural member.

FIG. 8. A view of a solid state thermoelectric device attached to the UVC lamp.

DETAILED DESCRIPTION OF THE INVENTION

Figure 1:
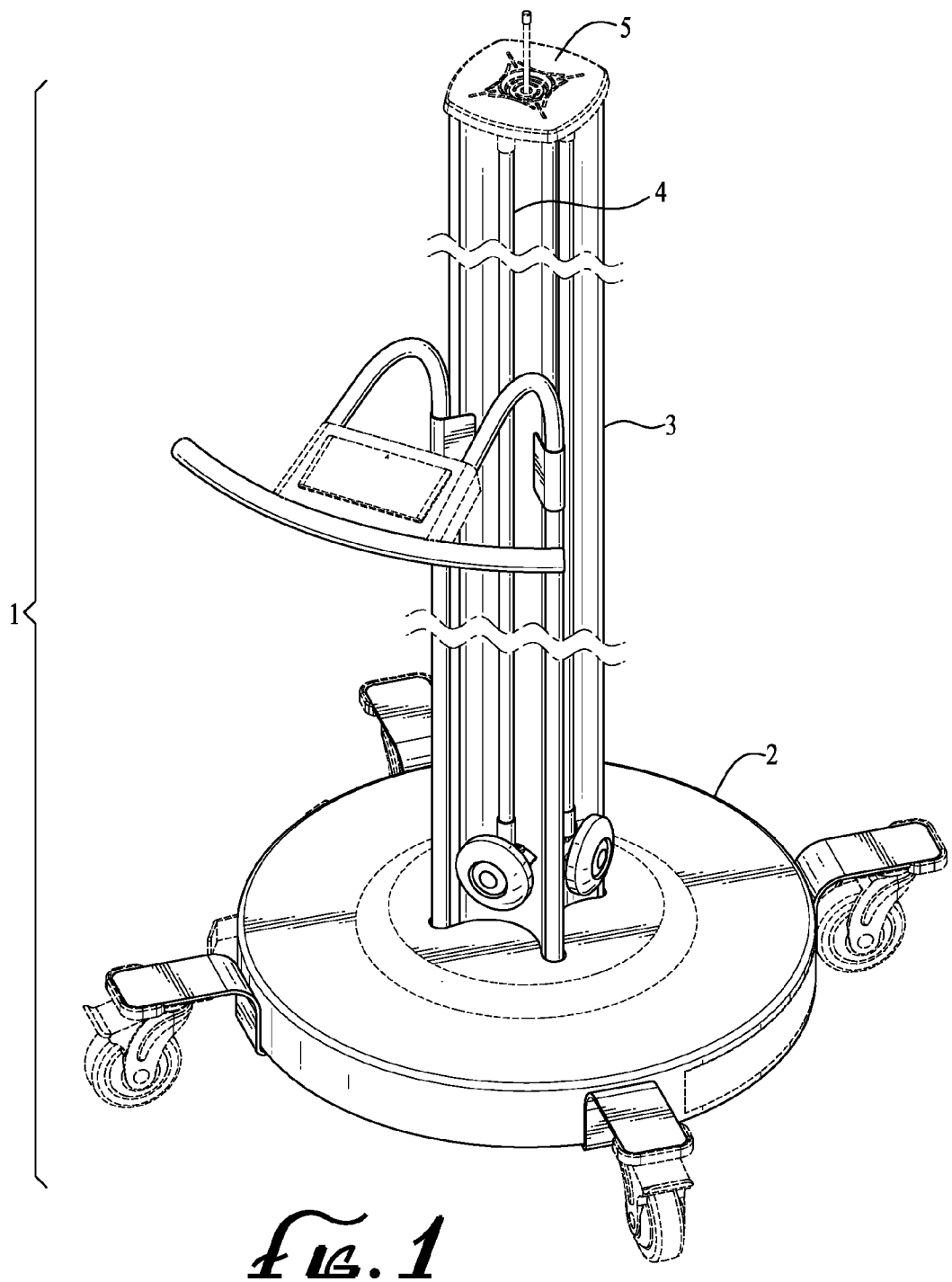
FIG. 1. An isometric drawing of one preferred embodiment of the UVC device utilizing this invention.

Referring to FIG. 1, a typical device 1 for the UV disinfection of air or surfaces is shown. The basic elements of the device are a base 2, a support, in this case, acting also as a conduit 3 and an opening 5 for the exit of air. One or more lamps 4 are installed around the support or conduit 3.

Figure 2:
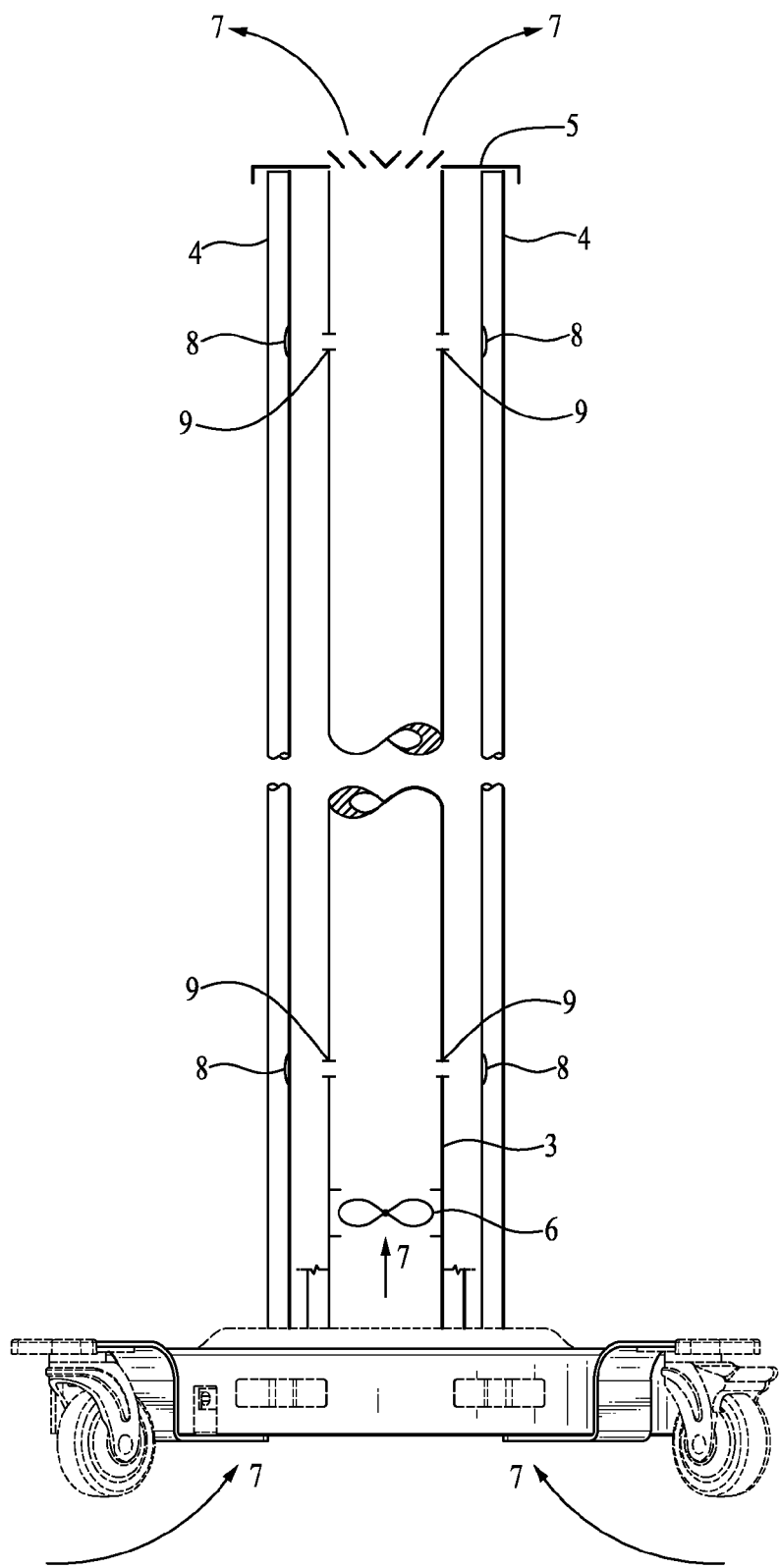
FIG. 2. A vertical cross sectional view of the device shown in FIG. 1

FIG. 2 shows the typical device 1, in cross section. An air moving device 6, including without limitation a fan or blower, is installed in the conduit 6 or may be installed in the base 2. The air moving device 6 causes air 7 to move into the conduit 3 and much of the air to exit through opening 5. Orifices, openings or holes 9 of a specific pre-determined diameter are placed in the conduit 4 at a strategic point selected to direct the air 7 through the orifices 9 to an area near or at the critical spot or points 8 (including mercury spot or amalgam spot, which contains mercury) on the lamp 4.

In another embodiment, not shown, the opening 5 may be omitted allowing all the air 7 to be directed through the orifices 9. In yet another embodiment (not shown), a multitude of small conduits could be used to individually supply air 7 to orifices 9.

Figure 3A:
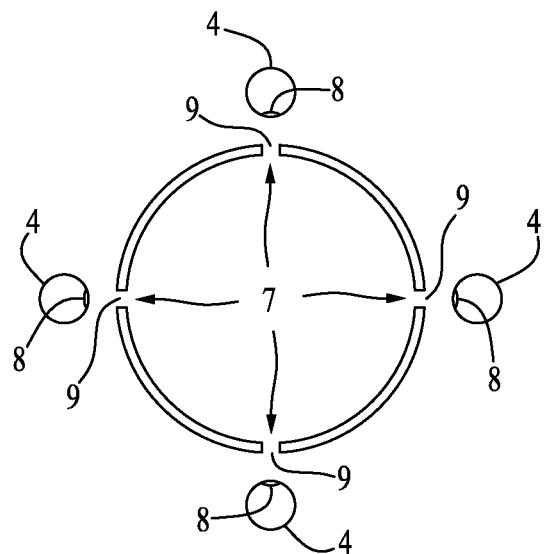
FIG. 3a. A horizontal cross sectional view of the device shown in FIG. 1 (enlarged).
Figure 3B:
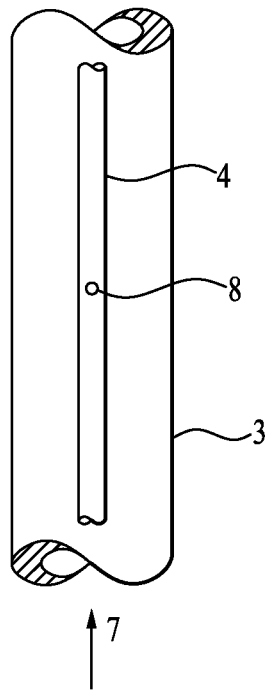
FIG. 3b. An enlarged portion of the conduit 3, shown in FIG. 2.
Figure 3C:
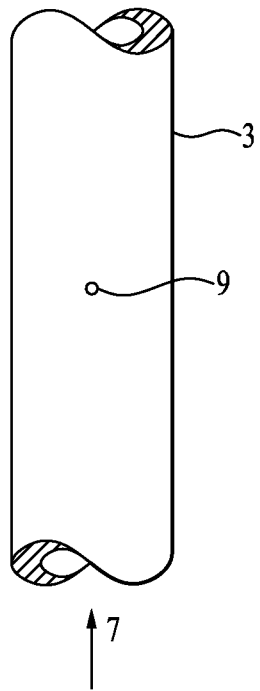
FIG. 3c. The view shown in FIG. 3b with the lamp 8 removed for clarity.

FIG. 3a shows a horizontal cross sectional view through the conduit 3. Air 7 flows through the orifices 9 and is directed to the critical spot 8 on the lamp 4. FIG. 3b shows a portion of the conduit 3 with the lamp 4. In FIG. 3c, the lamp 4 is removed to better show one of the orifices 9.

Figures 4A, 4B:
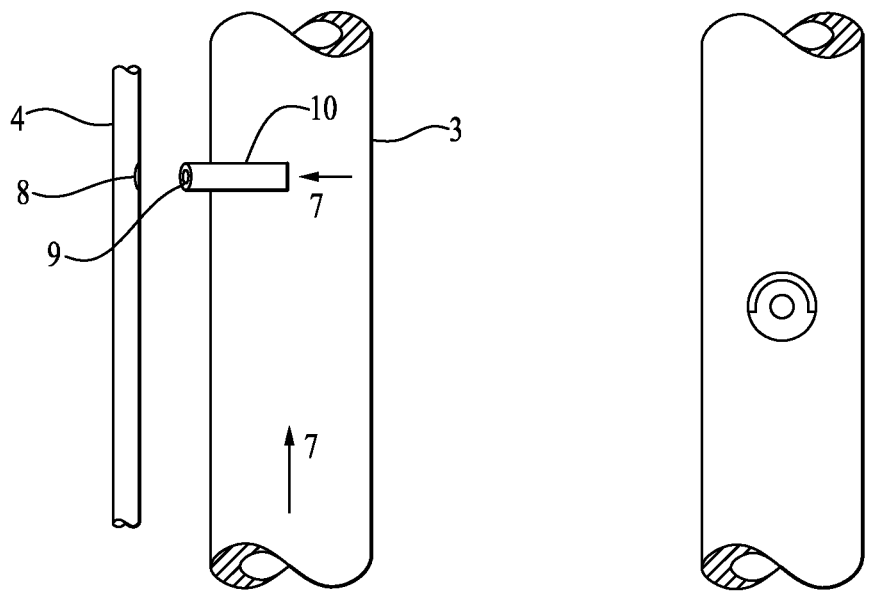
FIG. 4a. A view of an alternate embodiment showing use of an additional component to direct air.
FIG. 4b. A view of the additional component of FIG. 4a from inside the conduit 3.
Figure 4C:
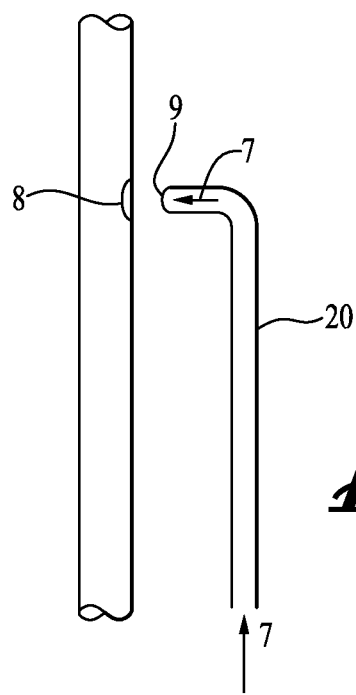
FIG. 4c. A view of an individual conduit (alternate embodiment)

An alternate embodiment of this invention is shown in FIG. 4a which shows a portion of the conduit 3 with a diverter or nozzle 10 installed in the conduit 3 to improve air flow to the critical spot 8. The nozzle/diverter 10 contains the proper size orifice 9. FIG. 4b shows a view of the nozzle/diverter 10 from inside the conduit. An alternate embodiment for delivering cooling air 7 to the critical spot 8 is shown in FIG. 4c and it consists of one or more individual conduits 20 for each critical spot 8.

Figure 5:
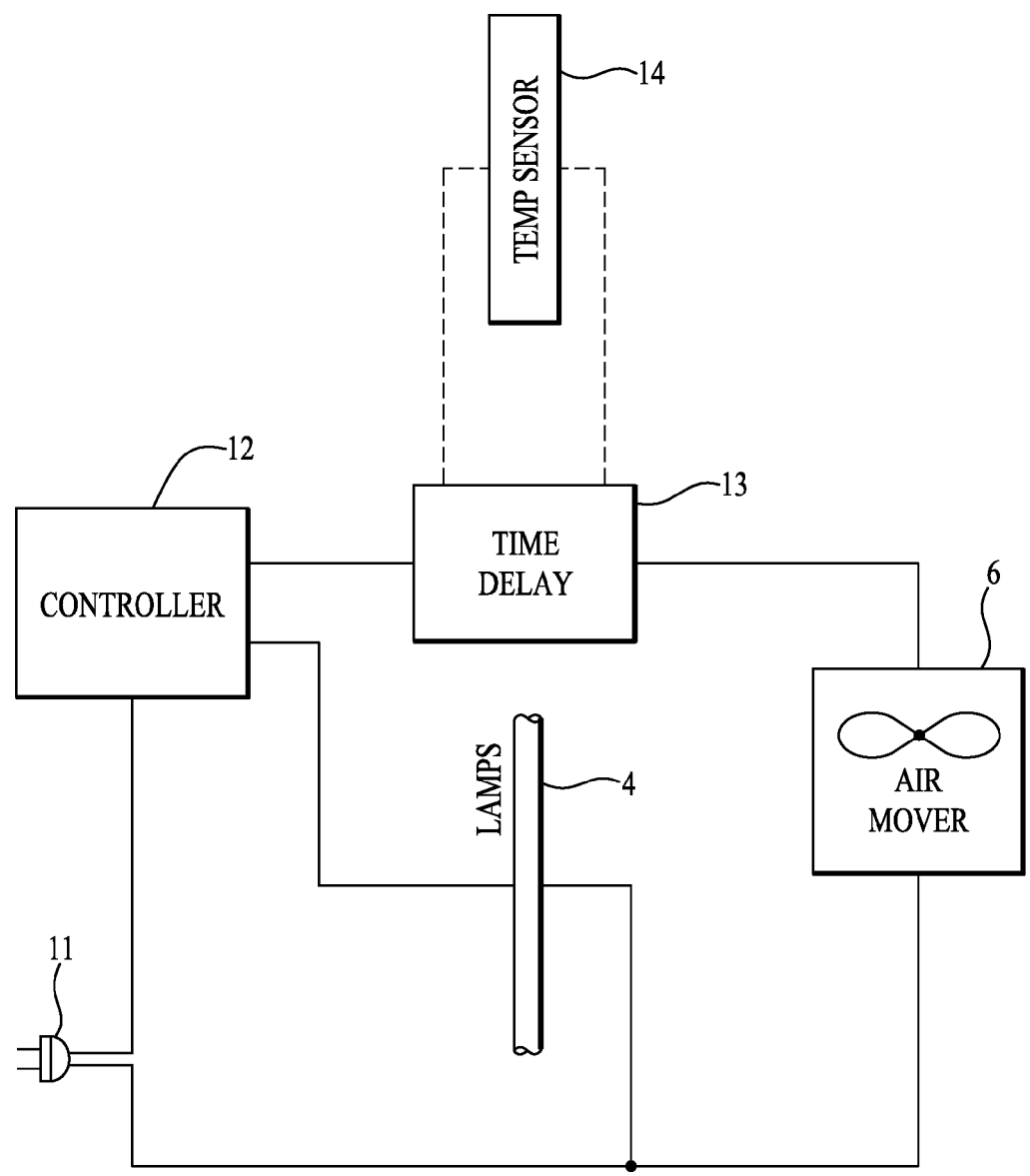
FIG. 5. A schematic showing a control circuit for controlling operation of the air moving component.

Often, it is advantageous to allow the lamp to come up to the proper temperature rapidly prior to applying cooling air 7. A means (a part of this invention) is shown to delay operation of the air moving device 6 is shown in FIG. 5; a delay operation is useful to allow the UV lamp to reach a preferred operating temperature. Alternatively, this may also power a thermo electric cooling device 17. A source of power 11 powers a main controller 12, which normally operates the lamps 4 and the air mover 6, as appropriate. A hardware or software time delay 13 is located in the control circuit, such that operation of the air mover 6 can be controlled or delayed. Optionally, a temperature sensor 14 may be added to the time delay 13 or controller 12 to control operation of the air mover 6.

Alternate methods (another part of this invention) to remove heat from the critical spots 8 of the lamp 4 are shown in FIGS. 6 and 7. A heat sink collar 15 may be applied to the lamp 4 around the critical spot 8. Heat is transferred from the critical spot 8 to the ambient air. The heat sink 15 may or may not be additionally cooled with air from the orifices 9. In another embodiment, the heat sink 16 is larger and contacts a support 19 in the apparatus to further draw heat from the critical spot 8.

In yet another embodiment of the invention, shown in FIG. 8, a thermoelectric cooling/heating device 17 is used to control the temperature of the critical spots 8. The temperature of the thermoelectric heating/cooling device 17 and the heat controlling capacity may be controlled by a controller 18.

An apparatus for disinfection of air and surfaces, comprising:
A UV lamp having a mercury amalgam spot;
A power source;
A conduit body, which has at least one hole that is located near the mercury spot of the UV lamp; and
An air moving device, which delivers air through the at least one hole in the conduit body and near the mercury spot of the UV lamp,
Whereby the air moving device provides cooling to alter temperature near the mercury amalgam spot of the UV lamp.

The apparatus further comprises at least one hole is an air director, which is located near the mercury amalgam spot of the UV lamp; a controller is used to modulate speed of the air moving device in order to maintain the temperature of the UV lamp; the controller uses a temperature sensor located near the mercury amalgam spot to maintain the temperature of the UV lamp; the mercury amalgam spot comprises, mercury or an amalgam; the air moving device keeps the mercury amalgam spot below its melting temperature; the air moving device keeps the mercury amalgam spot between 80 degrees C. and 150 degrees C.; the air director is a nozzle, an orifice or a diverter; the controller has a delay function to delay operation of the air moving device, in order to allow the UV lamp to reach an operating temperature.

An apparatus for disinfection of air and surfaces, comprising:
A UV lamp having a mercury amalgam spot;
A power source;
A thermo-electric device, which is in contact with the UV lamp near the mercury amalgam spot, whereby the thermo-electric device allows for heating or cooling to the mercury amalgam spot of the UV lamp.

The apparatus further comprising the thermo-electric device uses a temperature sensor located near the mercury amalgam spot of the UV lamp; the mercury amalgam spot comprises, mercury or an amalgam; the thermo-electric device keeps the mercury amalgam spot below its melting temperature; the thermo-electric device keeps the mercury amalgam spot between 80 degrees C. and 150 degrees C.; there is an air moving device, which directs air through at least one hole near the mercury amalgam spot of the UV lamp.

An apparatus for disinfection of air and surfaces, comprising:
A UV lamp having a mercury amalgam spot;
A power source; and
A heat sink, which is in contact with the UV lamp near the mercury amalgam spot, whereby the heat sink allows for heat dissipation from the UV lamp.

The apparatus further comprising: the heat sink is connected to an adjacent structural component of the apparatus to increase the heat dissipation from the UV lamp; the mercury amalgam spot comprises, mercury or an amalgam; the heat sink keeps the mercury amalgam spot below its melting temperature; the heat sink keeps the mercury amalgam spot between 80 deg. C. and 150 deg. C.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Further, the title, headings, terms and phrases used herein are not intended to limit the subject matter or scope; but rather, to provide an understandable description of the invention. The invention is composed of several sub-parts that serve a portion of the total functionality of the invention independently and contribute to system level functionality when combined with other parts of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6.

Incorporation by reference: All publications, patents, and patent applications mentioned in this specification are herein incorporated by reference to the same extent as if each individual publication, patent, or patent application was specifically and individually indicated to be incorporated by reference, including: US 2012/0305787A1 (Henson); U.S. Pat. No. 8,575,567B2 (Lyslo); U.S. Pat. No. 7,658,891B1 (Barnes); US 2005/0258378A1 (Speer).

What is claimed is:

1. An apparatus for disinfection of air and surfaces, comprising:
   A UV lamp having a mercury amalgam spot;
   A power source;
   A conduit body, which has at least one hole that is located near the mercury spot of the UV lamp; and
   An air moving device, which delivers air through the conduit body in a first direction; and the at least one hole directs the air in a second direction and near the mercury spot of the UV lamp,
   Whereby the air moving device provides cooling to alter temperature near the mercury amalgam spot of the UV lamp.

2. The apparatus of claim 1, wherein the at least one hole is an air director, which is located near the mercury amalgam spot of the UV lamp.

3. The apparatus of claim 2, wherein the air director is a nozzle, an orifice or a diverter.

4. The apparatus of claim 1, wherein a controller is used to modulate speed of the air moving device in order to maintain the temperature of the UV lamp.

5. The apparatus of claim 4, wherein the controller uses a temperature sensor located near the mercury amalgam spot to maintain the temperature of the UV lamp.

6. The apparatus of claim 4, wherein the controller has a delay function to delay operation of the air moving device, in order to allow the UV lamp to reach an operating temperature.

7. The apparatus of claim 1, wherein the mercury amalgam spot comprises, mercury or an amalgam.

8. The apparatus of claim 1, wherein the air moving device keeps the mercury amalgam spot below its melting temperature.

9. The apparatus of claim 1, wherein the air moving device keeps the mercury amalgam spot between 80 degrees C. and 150 degrees C.

10. An apparatus for disinfection of air and surfaces, comprising:
    A UV lamp having a mercury amalgam spot;
    A power source;
    A conduit body, which has at least one hole that is located near the mercury spot of the UV lamp; and
    An air moving device, which delivers air through the conduit body in a first direction;
    and the at least one hole directs the air in a second direction and near the mercury spot of the UV lamp;
    A controller is used to modulate speed of the air moving device in order to maintain the temperature of the UV lamp; the controller has a delay function to delay operation of the air moving device, in order to allow the UV lamp to reach an operating temperature;
    Whereby the air moving device provides cooling to alter temperature near the mercury amalgam spot of the UV lamp.

11. The apparatus of claim 10, wherein the at least one hole is an air director, which is located near the mercury amalgam spot of the UV lamp.

12. The apparatus of claim 10, wherein the controller uses a temperature sensor located near the mercury amalgam spot to maintain the temperature of the UV lamp.

13. The apparatus of claim 10, wherein the mercury amalgam spot comprises, mercury or an amalgam; and the air moving device keeps the mercury amalgam spot between 80 degrees C. and 150 degrees C.

14. An apparatus for disinfection of air and surfaces, comprising:
    A UV lamp having a mercury amalgam spot;
    A power source;
    A conduit body, which has at least one air director that is located near the mercury spot of the UV lamp; and
    An air moving device, which delivers air through the conduit body in a first direction;
    and the at least one air director directs the air in a second direction and near the mercury spot of the UV lamp;
    A controller is used to modulate speed of the air moving device in order to maintain the temperature of the UV lamp; the controller has a delay function to delay operation of the air moving device, in order to allow the UV lamp to reach an operating temperature;
    Whereby the air moving device provides cooling to alter temperature near the mercury amalgam spot of the UV lamp.

15. The apparatus of claim 14, wherein the controller uses a temperature sensor located near the mercury amalgam spot to maintain the temperature of the UV lamp.

16. The apparatus of claim 14, wherein the mercury amalgam spot comprises, mercury or an amalgam; and the air moving device keeps the mercury amalgam spot between 80 degrees C. and 150 degrees C.

* * * * *